United States Patent [19]

Hecmati

[11] Patent Number: 4,469,676

[45] Date of Patent: Sep. 4, 1984

[54] METHOD FOR ELIMINATING WRINKLES OCCURRING IN THE HUMAN SKIN

[76] Inventor: Michel Hecmati, 10697 Somma Way, Los Angeles, Calif. 90077

[21] Appl. No.: 506,428

[22] Filed: Jun. 21, 1983

[51] Int. Cl.³ .............................................. A61K 35/32
[52] U.S. Cl. ...................................................... 424/95
[58] Field of Search .......................................... 424/95

[56] References Cited
U.S. PATENT DOCUMENTS 3,476,855  11/1969  Balassa .................................. 424/95
3,966,908   6/1976  Balassa .................................. 424/95
4,350,682   9/1982  Balassa .................................. 424/95

*Primary Examiner*—Sam Rosen
*Attorney, Agent, or Firm*—Poms, Smith, Lande & Rose

[57] ABSTRACT

A composition which is injectable from a syringe and a method for using the composition to eliminate wrinkles of the skin. The composition contains sterile cartilage particles, which are non-absorbable by the human body, and which are uniformly dispersed in a liquid. The composition is used by injecting it, with a syringe, directly under the area where the wrinkle occurs.

8 Claims, No Drawings

METHOD FOR ELIMINATING WRINKLES OCCURRING IN THE HUMAN SKIN

BACKGROUND OF THE INVENTION

The skin of humans, particularly in the area of the face, will form wrinkles, particularly as a person grows older and/or is subject to exposure to direct sunlight. Even though the formation of such wrinkles have no physiological significance, they nevertheless may pose serious psychological problems to the person having them. In many societies persons do not like to show signs of aging and wrinkles are one of the primary signs of the aging process. Accordingly, preventing and/or eliminating wrinkles has been a major preoccupation of the human race since time immemorial. However, to date no truly satisfactory composition and/or method is known which will eliminate wrinkles and which does not suffer some decided disadvantage.

Among classic treatments for eliminating wrinkles there may be mentioned cutaneous aesthetic surgery which, although eliminating wrinkles, suffers numerous disadvantages including scarring of the skin, such scars being oftentimes difficult to conceal. Other methods for eliminating wrinkles include grafting of tissue which can be derived from a species different from that of the subject or which can be derived from tissue belonging to the same species as the subject. The former leads to a rejection of the tissue and the latter, although oftentimes not being subject to a rejection reaction, nevertheless leaves a scar where the tissue has been removed.

Other methods for eliminating wrinkles have included implantations from such diverse material as placentas, silicons, paraffin, vitamins, etc. The disadvantages of such implants are numerous and include rejection, allergic reactions and/or the effectiveness is limited to a restricted area.

The present invention obviates the disadvantages of the prior art methods discussed above by utilizing and implanting a composition under the area of the skin where the wrinkles occur, said composition being substantially non-absorbable and not subject to rejection or allergic reaction. The composition of the present invention is an injectable paste composed of finely divided particles of sterile cartilaginous tissue which is non-absorbable by the human body.

It is surprising that an injectable paste of divided particles of cartilaginous tissue are not absorbed by the human body even though dry powdered cartilage has been used heretofore in, for example, treating wounds. For example, U.S. Pat. No. 3,400,199 (Balassa) discloses utilizing powdered cartilage or the extract therefrom for healing wounds, said cartilage being taken from partially calcified skeletons of fetal origin or from very young or newly born animals such as calves.

The Balassa patent discloses removing tracheas of healthy adult beef cattle and digesting such trachea in an acetic acid and pepsin solution. The acid-pepsin solution is then removed by washing and the cartilage dried in a vacuum. The dry cartilage is then defatted by a solvent such as hexane and the dried and defatted cartilage granulated. The granulated cartilage was then ground to a fine powder and applied to wounds. Such cartilage, which has been altered from its natural state by drying and grinding to less than 40 microns is not suitable for preventing wrinkles because such cartilage will be absorbed by the human body in a very short period of time.

As noted above, the cartilage of the present invention is substantially non-absorbable by the human body when injected into or immediately under the skin. By substantially non-absorbable, I mean that very little of the cartilage, e.g. less than twenty percent of the cartilage, will be absorbed by the human body within one year after its injection under the area of the wrinkle in the skin which is being eliminated.

SUMMARY OF THE INVENTION

As noted above, the present invention relates to a method and composition which will eliminate wrinkles in the skin of humans. The composition is used by injecting the composition immediately under the area of the skin where the wrinkle occurs. Such injectable composition is substantially non-absorbable by the human body and will not be rejected by the human nor will it be subject to any allergy reactions. Moreover, the injection is easily and safely given without the necessity for anesthesizing the patient.

The cartilage used in the present invention may be derived from any animal source, including mammals, fish and birds. It is preferred if the cartilage is derived from a growing animal since the amount of cartilage in any animal is reduced the older the animal is. The most preferred animal is a bovine or ovine, particularly a calf or growing sheep. The most preferred cartilage is obtained from the ribs of a mammal, such as a calf.

I have used natural cartilage, which has not been altered as an implant. Such implants were not absorbed by the body but also could not be injected using a syringe. However, as demonstrated by the Balassa patent, cartilage which has been altered may become absorbable by the human body. Why this is so is not completely known. It may be that the cartilage was allowed to become dry. In any event, the cartilage of the present invention, which is not allowed to become dry and which is in a physical form which allows it to be injected using a syringe is neither substantially absorbed nor rejected by a human.

Animal cartilage, which has been cleaned to remove all other material from it, such as other connective tissue, fatty tissue, etc. contains a certain amount of water which may be removed by drying above 100° C. but below a temperature which the solid material will decompose. In general, such water will constitute from about 5 weight percent to about 15 weight percent of the clean cartilage. In my invention it is important, when processing the cartilage and prior to using the cartilage to eliminate wrinkles, that a substantial portion of this water not be removed. For example, it is preferred if the cartilage has, at all times prior to use, at least about 3 weight percent water. Since the cartilage of the present invention is in finely divided form, it is necessary to grind it. Precautions are taken to insure that there is no substantial loss of water during either the cleaning or the processing of the cartilage.

DESCRIPTION OF THE PREFERRED EMBODIMENTS

As noted above, the cartilage of the present invention may be derived from any animal source, the preferred animal source being a growing mammal such as a bovine or ovine. The most preferred animal source of the cartilage is a young calf, particularly the cartilage derived from the ribs.

To obtain the rib cartilage, the calf is slaughtered and the ribs removed. As much of the extraneous tissue, bones, etc. are removed manually and the remaining cartilage is then, preferably, cut up into relatively small pieces, say from an inch to five inches or more. The partially cleaned cartilage is then more thoroughly cleaned by placing the cartilage in a cleaning solution, preferably a solvent for animal fats, etc. which will dissolve and/or remove the remaining extraneous tissue, it being important that the solution not remove a substantial amount of water of the cartilage. Cleaning solutions and or solvents for removing the extraneous tissue are, in general, known in the art and include aqueous acetic acid and ethanol, it being important that when using, for example, ethanol that it not be so concentrated as to remove a substantial amount of the water from the cartilage, for example, the amount of water lost should not exceed that amount that when the cartilage is ground it will be dry rather than a paste or gel. In the case of using ethanol it is preferred that the ethanol be mixed with water so that there are equal volumes of water and ethanol in the composition. It is even more preferred that when the cartilage is cleaned that a certain amount of an aqueous saline solution be present in order to insure that the cartilage remains in its natural state.

In one of the presently preferred embodiments the calf cartilage, after removal, was cut into small pieces (e.g. varying from about one inch to five or more inches). The cut cartilage was then placed in a liquid composition containing equal volumes of a 0.9 weight percent aqueous saline solution (physiological or isotonic saline solution) and 90 percent volume ethanol and 10 percent volume water.

The cartilage was allowed to remain in the ethanol-aqueous solution at ambient temperature until substantially all of the extraneous tissue was removed therefrom, approximately thirty days. However, as noted, the solution could be aqueous acetic acid or other compositions known to remove and/or dissolve the extraneous tissue.

After the thirty day period the cartilage was washed with an isotonic saline solution (purified water containing 0.9 weight percent sodium chloride) until all of the ethanol was removed.

The pure and sterile cartilogenous tissue was then ground in a standard porcelain ball mill half-filled with metal balls under sterile conditions until the largest of the particles were smaller than and would pass through the smallest available standard medical syringes. For example, the cartilage particles may range from about 5 to about 100 or 150 Tyler mesh.

It is believed to be important during the grinding of the cartilage that the cartilage not be allowed to become dry. If necessary during the grinding, purified water will be added in order that the amount of water of the cartilage not be substantially reduced, e.g. the cartilage will have at least three to five weight percent. It is preferred if the water added during grinding also contains sodium chloride, for example the concentration of the sodium chloride may range from 0.5 to 5 weight percent and preferably the aqueous saline solution will be an isotonic or physiological solution.

The cartilage is ground to the suitable particle size, under sterile conditions (e.g. under a blanket of ozone) and under conditions insuring that the moisture content is not substantially reduced. If necessary, an aqueous liquid is added to insure the proper moisture content.

During grinding some of the water is released from the cartilage. The ground cartilage is in the form of a viscous paste wherein the particles are uniformly dispersed throughout the liquid and are relatively soft and pliable which is very helpful in insuring that the composition will pass through the injectable opening of a syringe. Thus this composition per se may be injected into the appropriate area of a human to eliminate wrinkles. It is, however, preferred if a slight amount of a non-toxic liquid is added in order to maintain the cartilage particles relatively soft and pliable. It is even more preferred if the non-toxic liquid is a non-toxic aqueous liquid (e.g. a non-toxic aqueous saline solution containing from 0.5 weight percent to 15 weight percent sodium chloride) so that during storage the resulting composition will not have less than about 5 weight percent moisture, including that absorbed in the cartilage. In general, the composition will contain from about 95 weight percent to about 80 or 85 weight percent cartilage particles. Since some of the liquid may be absorbed by the body it is preferred that the composition not contain less than about 80 weight percent cartilage and more preferably not less than about 85 weight percent cartilage.

The thus formed injectable composition is used to eliminate wrinkles by placing the composition in a suitable syringe and then injecting the composition immediately under the entire length of the wrinkle desired to be eliminated. Generally, it is preferred in the first injection to use slightly less of the composition than the amount necessary to completely eliminate the wrinkle. After about a month or so the patient is re-examined to determine if the wrinkle has been substantially eliminated. If not, an additional amount of my composition is injected under the wrinkle so that the skin is smooth. The attending physician can easily ascertain the amount of injectable composition to be used since the injection or injections will be in an amount sufficient to eliminate the wrinkle. Based upon clinical observation the wrinkle will not return for a long period of time nor will the implant be absorbed by the human body. I have experience with implants lasting a year or more and to date no implant has had to be replaced.

In order to more fully explain and illustrate the present invention the following examples are given.

EXAMPLE 1

A female patient with a superficial (epidermal) face wrinkle was injected with 0.2 cc of a composition containing 90 weight percent sterile, non-absorbable cartilage particles, the size of the particles being as such that they were less than and would pass through the opening of the syringe, and 10 weight percent of an 0.9 percent saline solution (hereinafter such composition is referred to as "Cartiladerm"). The Cartiladerm composition was injected into the skin directly underneath the wrinkle and along the wrinkle's entire length, the skin having been cleaned with alcohol and numbed by chilling the skin with an ice cube rubbed over the face. If desired, although not necessary, the injection is followed with a finger massage of the cartiladerm located under the wrinkle.

As a result of the injection the skin where the wrinkle had been previously was substantially smooth and the wrinkle disappeared. The treatment was repeated a month later except, in this instance, 0.1 cc of the Cartiladerm was used and this time the wrinkle completely disappeared. The woman patient has been free of this particular wrinkle for over a year and it is expected that the wrinkle will not reappear for an indefinite period of time.

EXAMPLE 2

A female patient was treated whose face had a deep face wrinkle. She was injected with 0.5 cc of Cartiladerm directly under the area of the deep face wrinkle (a subdermal injection). Prior to the injection the skin around the wrinkle had been cleansed with alcohol and the skin had been rubbed with ice to chill it. Immediately after the injection the skin where the wrinkle had previously been was substantially smooth.

The same patient, six weeks later, had another injection of Cartiladerm using the same procedure as indicated above except that only 0.2 cc of the Cartiladerm was used. This time the wrinkle was completely eliminated and has not reappeared for over a year.

The foregoing examples are given solely for purposes of illustration and are not to be considered limiting.

I claim:

1. A method for eliminating wrinkles in the skin of humans which comprises:

injecting, with a syringe, a syringe injectable composition which is substantially non-absorbable by the human body, directly under the area where said wrinkle occurs along substantially its entire length, the amount of said syringe injectable composition injected being substantially sufficient to smooth the skin where the wrinkle exists, said syringe injectable composition consisting essentially of sterile cartilage particles which are substantially non-absorbable by the human body, the size of said sterile, non-absorbable cartilage particles being such that the largest of said particles are smaller than and will flow through the injectable opening of said syringe.

2. A method according to claim 1 wherein said sterile, non-absorbable cartilage particles are uniformly dispersed throughout a non-toxic liquid, said sterile non-absorbable cartilage particles being present in an amount of between about 80 weight percent and 95 weight percent.

3. A method according to claim 2 wherein said non-toxic liquid is a non-toxic aqueous liquid.

4. A method according to claim 3 wherein said non-toxic aqueous liquid is a non-toxic aqueous saline solution.

5. A method according to claim 4 wherein said non-toxic aqueous saline solution consists essentially of water and from about 0.5 weight percent to about 5 weight percent sodium chloride.

6. A method according to claim 5 wherein said non-toxic aqueous saline solution is a physiological saline solution.

7. A method according to claim 1 wherein the largest of said sterile, non-absorbable cartilage particles are less than about 5 Tyler mesh.

8. A method according to claim 1 wherein said sterile, non-absorbable cartilage particles have never been dry.

* * * * *